US006399833B1

(12) United States Patent
Kurihara et al.

(10) Patent No.: US 6,399,833 B1
(45) Date of Patent: Jun. 4, 2002

(54) PROCESS FOR PRODUCING ARYL VINYL SULFONE SOLUTION AND USE THEREOF

(75) Inventors: Akio Kurihara, Toyonaka; Isao Kurimoto, Suita; Naoyuki Takano, Ibaraki, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/601,235

(22) PCT Filed: Feb. 8, 1999

(86) PCT No.: PCT/JP99/00542

§ 371 (c)(1),
(2), (4) Date: Jul. 31, 2000

(87) PCT Pub. No.: WO99/40065

PCT Pub. Date: Dec. 8, 1999

(30) Foreign Application Priority Data

Feb. 9, 1998 (JP) .............................. 10-27119
Oct. 2, 1998 (JP) ........................... 10-281125
Oct. 2, 1998 (JP) ........................... 10-281126

(51) Int. Cl.$^7$ ............................................ C07C 315/06
(52) U.S. Cl. .............................. 568/28; 568/33; 568/35
(58) Field of Search .............................. 568/28, 30, 32, 568/33, 34, 35

(56) References Cited

U.S. PATENT DOCUMENTS 3,242,041 A * 3/1966 Aichenegg et al.
3,578,717 A * 5/1971 Mitsch et al.
4,335,142 A * 6/1982 Relyea et al.
4,386,221 A * 5/1983 Hyatt et al. .................... 568/28
4,517,384 A * 5/1985 Brace et al. .................... 568/27
5,902,905 A    5/1999 Seko et al.

FOREIGN PATENT DOCUMENTS

| DE | 842198 | 6/1952 |
| DE | 877607 | 7/1953 |
| JP | A62132865 | 6/1987 |
| JP | A1036337 | 2/1998 |
| JP | A10195039 | 7/1998 |

OTHER PUBLICATIONS

Steven C. DeVito, Chemtech, Nov. 1996, pp. 34–47.
A. H. Ford–Moore et al., J. Chem Society, 1949, pp. 1754–1757.
Richard V.C. Carr, J. Org. Chem. vol. 48, No. 25, 1983, pp. 4976–4986.
David J. Ager, J. Chem. Soc. Chem. Commun., 1984, pp. 486–488.
Sergio Cossu et al., Synthetic Communications, 26(2), 1996, pp. 211–216.
Jae Wook Lee et al., Bull. Korean Chem. Soc., 1995, vol. 16, No. 7, pp. 670–672.
Neal O. Brace, J. Org. Chem. vol. 58, No. 16, 1993, pp. 4506–4508.

* cited by examiner

Primary Examiner—Jean F. Vollano
(74) Attorney, Agent, or Firm—Birch, Stewart, Kolasch & Birch, LLP

(57) ABSTRACT

A process for producing a purified aryl vinyl sulfone solution, characterized in that an aryl vinyl sulfone is crystallized from an organic solvent solution of a crude aryl vinyl sulfone to give a crystallization mixture, and a wet cake of the aryl vinyl sulfone obtained by the separation of the solution from the said mixture is dissolved in a solution-forming solvent selected from ethers of 4 to 8 carbon atoms, aromatic hydrocarbons of 6 to 10 carbon atoms, halogenated hydrocarbons of 1 to 6 carbon atoms, ketones of 3 to 8 carbon atoms, esters of 3 to 6 carbon atoms, and nitrites of 2 to 6 carbon atoms.

9 Claims, No Drawings

PROCESS FOR PRODUCING ARYL VINYL SULFONE SOLUTION AND USE THEREOF

This application is the national phase under 35 U.S.C. § 371 of PCT International Application No. PCT/JP99/00542 which has an International filing date of Feb. 8, 1999, which designated the United States of America.

TECHNICAL FIELD

The present invention relates to a process for producing an aryl vinyl sulfone solution, methods of transportation and storage of an aryl vinyl sulfone as a solution, and use thereof.

BACKGROUND ART

Aryl vinyl sulfones are useful compounds as intermediates of drugs or other products. The organic layers containing crude aryl vinyl sulfones, which can be obtained by various methods of production, may often be contaminated by impurities or the like in the production process, and it has been difficult to use these organic layers directly as intermediates of drugs or other products. Thus, there has been a need for the isolation of crystalline powder of aryl vinyl sulfones with low purity, which can be obtained by the concentration of the said organic layers, and for the subsequent purification of the crystalline powder by recrystallization or other techniques. At that time, one must handle the crystalline powder of aryl vinyl sulfones, so that some problems will be caused on the working atmosphere, such as dusting, from the viewpoints of safety and health. Therefore, handling methods without handling crystalline powder have been required.

In particular, phenyl vinyl sulfone as a typical compound has been known to exhibit irritation (Aldrich Material Safety Data). Further, it has been reported that one should pay attention for safety to the handling of vinylsulfonyl group-containing compounds (Chemtech, November, 34 (1996)). Therefore, the development of methods without handling solids of aryl vinyl sulfones, by which aryl vinyl sulfones can be handled safely and healthily, has been desired.

OBJECTS OF THE INVENTION

The main object of the present invention is to provide a method for handling aryl vinyl sulfones safely and healthily without handling solids of aryl vinyl sulfones.

This object and the other objects, as well as the advantages, of the present invention are explained below.

SUMMARY OF THE INVENTION

The present inventors have studied processes of production as well as methods of transportation and storage without handling powder of aryl vinyl sulfones, thereby completing the present invention.

That is, the present invention provides a process for producing a purified aryl vinyl sulfone solution, characterized in that an aryl vinyl sulfone is crystallized from an organic solvent solution of a crude aryl vinyl sulfone to give a crystallization mixture, and a wet cake of the aryl vinyl sulfone obtained by the separation of the solution from the said mixture is dissolved in a solution-forming solvent selected from ethers of 4 to 8 carbon atoms, aromatic hydrocarbons of 6 to 10 carbon atoms, halogenated hydrocarbons of 1 to 6 carbon atoms, ketones of 3; to 8 carbon atoms, esters of 3 to 6 carbon atoms, and nitriles of 2 to 6 carbon atoms; methods of transportation and storage of a purified aryl vinyl sulfone as a solution; and use thereof.

DETAILED DESCRIPTION OF THE INVENTION

First, the following explains a process for producing a purified aryl vinyl sulfone solution, characterized in that an aryl vinyl sulfone is crystallized from an organic solvent solution of a crude aryl vinyl sulfone to give a crystallization mixture, and a wet cake of the aryl vinyl sulfone obtained by the separation of the solution from the said mixture is dissolved in a solution-forming solvent selected from ethers of 4 to 8 carbon atoms, aromatic hydrocarbons of 6 to 10 carbon atoms, halogenated hydrocarbons of 1 to 6 carbon atoms, ketones of 3 to 8 carbon atoms, esters of 3 to 6 carbon atoms, and nitriles of 2 to 6 carbon atoms.

The organic solvent solution of a crude aryl vinyl sulfone as used in the present invention may include, for example, organic solvent solutions containing the crude aryl vinyl sulfone, which can be obtained by ordinary post-reaction treatments such as neutralization and water washing or by optional treatments such as desalting, from a reaction mixture obtained by the base treatment of a β-haloethyl aryl sulfone, a β-sulfate ethyl aryl sulfone, a β-tosyloxyethyl aryl sulfone, a β-mesyloxyethyl aryl sulfone or a β-nitrate ethyl aryl sulfone, or from a reaction mixture obtained by the oxidation of a vinyl aryl sulfide.

More particularly, the crude aryl vinyl sulfone in the present invention may include those containing a compound obtained by the treatment of a compound of formula (I):

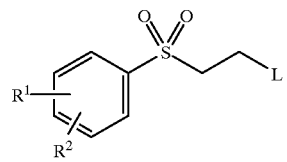

wherein $R^1$ and $R^2$ are the same or different and are independently hydrogen, halogen, lower alkyl, lower alkoxy, nitro, amino, lower alkylamino, or di(lower alkyl)amino, and L is a leaving group, with a base; or those containing a compound of formula (III):

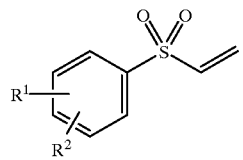

wherein $R^1$ and $R^2$ are as defined above, which is obtained by the oxidation of an aryl vinyl sulfide compound of formula (II):

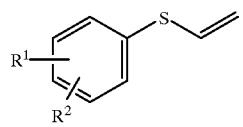

wherein $R^1$ and $R^2$ are as defined above.

The atoms or groups represented by $R^1$ or $R^2$ in formulas (I), (II), and (III) are defined as follows:

The halogen atom may include, for example, fluorine, chlorine, bromine, and iodine atoms;

The lower alkyl group may include, for example, straight chain or branched alkyl groups of 1 to 6 carbon atoms, such as methyl, ethyl, n-propyl, n-butyl, n-pentyl, i-propyl, i-butyl, sec-butyl, t-butyl, neopentyl, and n-hexyl groups.

The lower alkoxy group may include, for example, straight chain or branched alkoxy groups of 1 to 6, carbon atoms, such as methoxy, ethoxy, n-propoxy, n-butoxy, n-pentoxy, i-propoxy, i-butoxy, sec-butoxy, t-butoxy, neopentoxy, and n-hexyloxy groups.

The lower alkylamino group refers to an amino group substituted with one lower alkyl group, in which the lower alkyl group may include the same groups as described above. Examples of the lower alkylamino group are methylamino, ethylamino, and t-butylamino groups. The di(lower alkyl)amino group refers to an amino group substituted with two lower alkyl groups, in which the lower alkyl groups may include the same groups as described above. Examples of the di(lower alkyl)amino group are dimethylamino, diethylamino, methylethylamino, and t-butylmethylamino groups.

The leaving group represented by L in formula (I) may include sulfate ($OSO_3H$), nitrate ($ONO_2$), and sulfonyloxy (e.g., tosyloxy, mesyloxy) groups, and halogen (chlorine, bromine, iodine) atoms.

Specific compounds of formula (I) may include compounds containing the leaving groups as described above, respectively, in the following aryl vinyl sulfones.

The base for use in the treatment of a compound of formula (I) may include inorganic or organic bases, or mixtures thereof The inorganic base may be hydroxides (sodium hydroxide, potassium hydroxide, lithium hydroxide), or carbonates or bicarbonates (sodium carbonate, potassium carbonate, sodium hydrogencarbonate, potassium hydrogencarbonate), of alkali metals or alkaline earth metals.

The organic base may include mono-, di-, or trialkylamines (triethylamine) and pyridine compounds. For example, there can be mentioned the disclosures of [J. Org. Chem., 58, 4506 (1993), J. Chem. Soc., 1754 (1949)], [JP-A 10-251219], [German Patent No. 842,198 (1942)], [Bull. Korean Chem. Soc., 16, 670 (1995)], [JP-A 10-36337], and [JP-A 10-195039]; and methods in accordance with these disclosures.

The aryl vinyl sulfide of formula (II) may include aryl vinyl sulfide compounds corresponding to the aryl vinyl sulfones as described below.

Specific examples of the aryl vinyl sulfone are phenyl vinyl sulfone, (4-chlorophenyl) vinyl sulfone, (3,4-dichlorophenyl) vinyl sulfone, (4-bromophenyl) vinyl sulfone, (4-fluorophenyl) vinyl sulfone, (4-iodophenyl) vinyl sulfone, (4-methylphenyl) vinyl sulfone, (2,4-dimethylphenyl) vinyl sulfone, (4-ethylphenyl) vinyl sulfone, (4-i-butylphenyl) vinyl sulfone, (4-t-butylphenyl) vinyl sulfone, (4-methoxyphneyl) vinyl sulfone, (3,4-dimethoxyphenyl) vinyl sulfone, (4-t-butoxyphenyl) vinyl sulfone, (3-aminophenyl) vinyl sulfone, (3-methylaminophenyl) vinyl sulfone, (3-ethylaminophenyl) vinyl sulfone, (3-dimethylaminophenyl) vinyl sulfone, (3-dimethylaminophenyl) vinyl sulfone, and (3-nitrophenyl) vinyl sulfone.

The organic solvent used in the organic-solvent solution of the crude aryl vinyl sulfone, which is subjected to crystallization, is not particularly limited, but may include, for example, organic solvents selected from ethers of 4 to 8 carbons atoms, aromatic hydrocarbons of 6 to 10 carbon atoms, halogenated hydrocarbons of 1 to 6 carbon atoms, ketones of 3 to 8 carbon atoms, esters of 3 to 6 carbon atoms, and nitriles of 2 to 6 carbon atoms; and mixed solvents thereof The ethers of 4 to 8 carbon atoms may include, for example, diethyl ether, methyl t-butyl ether, dimethoxyethane, diglyme, and dibutyl ether.

The aromatic hydrocarbons of 6 to 10 carbon atoms may include, for example, toluene, xylene, benzene, ethylbenzene, cumene, cymene, and t-butylbenzene.

The halogenated hydrocarbons of 1 to 6 carbon atoms (straight chain or optionally branched alkyl groups, aromatic hydrocarbons) may include, for example, dichloromethane, 1,2-diclhloroethane, chloroform, chlorobenzene, and carbon tetrachloride.

The ketones of 3 to 8 carbon atoms nay include, for example, acetone, methyl ethyl ketone, methyl propyl ketone, methyl isobutyl ketone, diethyl ketone, cyclopentanone, cyclohexanone, 2-heptanone, and ethyl amyl ketone.

The esters of 3 to 6 carbon atoms may include, for example, ethyl acetate, methyl acetate, propyl acetate, isopropyl acetate, butyl acetate, isobutyl acetate, ethyl formate, isopropyl formate, ethyl propionate, and 2-methoxyethyl acetate.

The nitriles of 2 to 6 carbon; atoms may include, for example, acetonitrile, propionitrile, butyronitrle, valeronitrile, and capronitrile.

Specific examples of the organic solvent solution of the crude aryl vinyl sulfone are as follows:

For example, solutions obtained by the reaction of a β-haloethyl aryl sulfone with triethylamine in a hydrophobic aromatic hydrocarbon organic solvent such as benzene or tetrahydrofuran, or in an ether organic solvent, and the separation of resulting salts [J. Org. Chem., 58, 4506 (1993), J. Chem. Soc., 1754 (1949)];

Solutions obtained by the reaction of a β-haloethyl aryl sulfone with an aqueous alkaline metal salt solution in the presence of an amine in a hydrophobic hydrocarbon organic solvent such as toluene, and the separation of an aqueous layer [JP-A 10-251219];

Solutions obtained by the reaction of an aryl sulfonyl ethanol with sulfuric acid in a halogenated hydrocarbon solvent such as dichloromethane, the treatment with a base such as an aqueous sodium hydroxide solution, and the separation of an aqueous layer [German Patent No. 842,198 (1942)];

Solutions obtained by the reaction of an aryl sulfonyl ethanol with methane sulfonyl chloride in a halogenated hydrocarbon solvent such as dichloromethane, the addition of triethylamine and reaction therewith, the addition of water and phase separation [Bull. Korean Chem. Soc., 16, 670 (1995)];

Solutions obtained by the reaction of an aryl sulfonyl ethanol with fuming nitric acid in a halogenated hydrocarbon solvent such as chloroform, the treatment with a base such as an aqueous sodium hydroxide solution, and the separation of an aqueous layer [JP-A 10-36337]; and Solutions obtained by the treatment of an aryl sulfonyl ethanol with a chlorinating agent in a hydrophobic organic solvent such as toluene, base treatment, the addition of water and phase separation [JP-A 10-195039].

There can also be mentioned, for example, solutions obtained by the oxidation of an aryl vinyl sulfide with an aqueous hydrogen peroxide solution, the addition of an ether solvent such as diethyl ether, and water, and the separation of an aqueous layer [Org. Synth., 64, 157 (1985)].

For the organic solvent, preferably selected are those which make it easy to wash a wet cake after crystallization by combinations with a desired solution-forming solvent, or which they can easily be removed by making use of a difference in boiling point from the solution-forming solvent or the properties of exhibiting azeotropy therewith. They can be selected in the same manner as for the washing solvents as described below.

The method for crystallizing an aryl vinyl sulfone from a solution containing a crude aryl vinyl sulfone may include, for example, crystallization by cooling, crystallization by evaporation, and methods using an aryl vinyl sulfone-containing solution and a solvent in which the aryl vinyl sulfone is substantially insoluble (hereinafter referred to as a poor solvent). The aryl vinyl sulfone-containing solution may be subjected directly to crystallization treatment, or may be subjected to crystallization treatment after the removal by distillation of some of the solvent from the said solution.

For crystallization by cooling or crystallization by evaporation, the crystallization temperature, operational pressure, and other conditions may suitably be selected, depending on the concentration of an aryl vinyl sulfone in the crude aryl vinyl sulfone-containing solution, the solvent, and other factors.

When a crude aryl vinyl sulfone-containing organic solvent solution and a poor solvent are used, there may be used either a method in which the poor solvent is added to the said solution, or a method in which the said solution is added to the poor solvent, with the latter being preferred. The poor solvent may include, for example, aliphatic (straight chain or optionally branched, or cyclic) hydrocarbons of 5 to 10 carbon atoms, such as hexane, heptane, octane, cyclohexane, nonane, and decane. The amount of such a poor solvent to be used is usually at most 100 times greater by weight, preferably 0.5 to 50 times greater by weight, relative to the aryl vinyl sulfone contained in the said solution. The aryl vinyl sulfone crystals are usually deposited by mixing the aryl vinyl sulfone-containing organic solvent solution with the poor solvent. More aryl vinyl sulfone crystals may be deposited by further cooling.

The method for separating a solution from a crystallization mixture (slurry) containing aryl vinyl sulfone crystals, which is obtained by such a crystallization treatment, may include various methods usually used, such as transferring the slurry to a filtering module, followed by filtration, removing a supernatant from a crystallization vessel using a pump, and decanting a supernatant by tilting a crystallization vessel.

The solution formation of a wet cake of the aryl vinyl sulfone thus obtained can be carried out, for example, directly in the filtering module or crystallization vessel. Alternatively, it may also be achieved by transferring the wet cake from the filtering module to a subsequent dissolution tank and then adding a solution-forming solvent thereto.

The method of direct solution formation in a filtering module may include, for example, those by closing the liquid-drawing port of the filtering module, adding a solution-forming solvent into the filtering module, dissolving a wet aryl vinyl sulfone cake in the filtering module, and opening the liquid-drawing port to remove an aryl vinyl sulfone solution. The said solution formation treatment may be repeated, depending on the volume of the filtering module and the solubility of the aryl vinyl sulfone into the solution-forming solvent used. Further, after the drawing of a filtrate, the liquid-drawing line may be turned to another receiving vessel and kept open, in which state the solution-forming solvent is added into the filtering module and the wet aryl vinyl sulfone cake is formed into a solution, whereas the resulting solution is drawn.

When a wet cake of an aryl vinyl sulfone is transferred from the filtering module to another dissolution tank and formed into a solution by the addition of a solution-forming solvent, there can be mentioned, for example, a method in which the dissolution tank for the dissolution of the aryl vinyl sulfone has been previously connected to the cake-discharge port of the filtering module, and the filtered crystals are discharged from the cake-discharge port into the dissolution tank and formed into a solution by the addition of a dissolving solvent to the dissolution tank. The solution-forming solvent may have been previously charged into the dissolution tank. In the filtering module, some of the crystals sometimes remain undischarged, in which case the liquid-drawing port of the filtering module is closed, and a solution-forming solvent is charged into the filtering module, and the remaining crystals are dissolved, and the resulting solution is transferred from the cake-discharge port to the dissolution tank.

The addition of a solution-forming solvent may be carried out continuously or intermittently.

The solution-forming solvent may be an organic solvent selected from ethers of 4 to 8 carbon atoms, aromatic hydrocarbons of 6 to 10 carbon atoms, halogenated hydrocarbons of 1 to 6 carbon atoms, ketones of 3 to 8 carbon atoms, esters of 3 to 6 carbon atoms, and nitrile of 2 to 6 carbon atoms in the same manner as described above; or a mixed solvent thereof.

These organic solvents may suitably be selected, depending on, for example, the purposes of use of aryl vinyl sulfones. Among all these organic solvents are preferred ketones of 3 to 6 carbon atoms (particularly preferred are acetone, methyl ethyl ketone, methyl isobutyl ketone, or the like), which have high dissolubility for aryl vinyl sulfones; esters of 3 to 10 carbon atoms (particularly preferred is ethyl acetate or the like); and nitriles of 2 to 6 carbon atoms (particularly preferred is acetonitrile).

The amount of such a solution-forming solvent to be used may be any of the amounts enough to dissolve the crystals of aryl vinyl sulfones, and it may suitably be determined, depending on the solution-forming solvent used, the concentration of desired aryl :vinyl sulfone solutions, temperature, and other factors.

The temperature in the solution formation may be any of the temperatures at which aryl vinyl sulfones are dissolved in solution-forming solvents, and it may be usually 100° C. or lower, preferably 0° C. to 50° C.

According to such a series of operations, a purified aryl vinyl sulfone solution can be obtained. When the introduction into the said solution of a crystallization solution adhering in a very small amount to the aryl vinyl sulfone crystals is to be reduced, the aryl vinyl sulfone crystals filtered can also be washed with a washing solvent to remove the adhering mother liquid, thereby attaining solvent replacement in advance of the solution formation. When the crystallization solvent has a lower boiling point than that of the solution-forming solvent or exhibits azeotropy with the solution-forming solvent, washing is not necessarily needed.

The washing solvent may be any of the solvents by which the mother liquid adhering to the crystals can be removed. When incorporation into a purified aryl vinyl sulfone solution finally obtained is to be avoided, the same solvent as the solution-forming solvent is used, or a solvent which exhibits azeotropy with the solution-forming solvent or which has a lower boiling point than that of the solution-forming solvent is used, and finally, any other solvent than the solution-forming solvent can also be removed by the partial concentration of an aryl vinyl sulfone solution.

When as such a washing solvent, a poor solvent in which aryl vinyl sulfones are substantially insoluble is used for washing, the amount of such a washing solvent to be used is not particularly limited. When any other solvent is used for washing, the amount of such a washing solvent to be used is preferably set at the lowest amount needed for the removal of a mother liquid adhering to the crystals, and it is used after cooled, if necessary.

As examples of the solvent exhibiting azeotropy, there can be mentioned, for example, hexane or ethyl acetate as the solvent exhibiting azeotropy with acetonitrile; diisopropyl ether and hexane as the solvent exhibiting azeotropy with acetone; ethyl acetate and hexane as the solvent exhibiting azeotropy with ethyl methyl ketone; acetone, ethyl acetate, diisopropyl ether, and hexane as the solvent exhibiting azeotropy with chloroform; and hexane exhibiting azeotropy with ethyl acetate; and it can be selected from the combinations of these solvents. In addition, the solvent exhibiting azeotropy with the above solutions-forming solvent or the solvent having a lower boiling point than that of the above solution-forming solvent can be selected and used from the solvents as disclosed in "Shinpan Youzai Pocket Book (edited by Yuki Gosei Kagaku Kyokai, Ohmsha, Ltd., pp. 62–66", Kagaku Binran, Kiso-hen II, 5th edition, Maruzen, pp. 147–149, (L. H. Horsley, "Azeotropic Data-III", Advances in Chemistry Series, No. 116, American Chemical Society (1973), W. Malesinski, "Azeotropy", Interscience Pub. (1965)).

Operations on and after the step of separating the wet cake of an aryl vinyl sulfone and the solution from the crystallization mixture solution are preferably carried out in a closed system. Of course the operation of crystallization may also be carried out in a closed system. By doing so, handling of an aryl vinyl sulfone in powder form can be avoided.

The aryl vinyl sulfone solution thus obtained can be concentrated or diluted with an additional solution-forming solvent to prepare an aryl vinyl sulfone solution of a prescribed concentration.

The concentration temperature in the concentration of an aryl vinyl sulfone solution may suitably be selected, depending on the solvent system, and it may be usually 100° C. or lower, preferably 30–80° C. The operational pressure may be determined, depending on the concentration temperature.

When the wet cake of an aryl vinyl sulfone obtained by the separation of the solution from the crystallization solution of the aryl vinyl sulfone is washed with a solvent exhibiting azeotropy with the solution-forming solvent, or when the crystallization solvent exhibiting azeotropy with the solution-forming solvent, the said solution can be concentrated to remove the washing solvent or crystallization solvent by azeotropy and then adjusted to a prescribed concentration.

When the wet cake of an aryl vinyl sulfone obtained by the separation of the wet aryl vinyl sulfone cake and the solution is washed with a solvent having a lower boiling point than that of the solution-forming solvent, or when a solvent having a lower boiling point than that of the solution-forming solvent is used as a crystallization solvent, the said solution can be concentrated to remove the low boiling point washing solvent or crystallization solvent and then adjusted to a prescribed concentration.

The concentration of an aryl vinyl sulfone in the aryl vinyl sulfone solution may suitably be selected, depending on the kind of organic solvent forming the said solution, and the range of temperature in the atmosphere for ordinary usage, storage, or transportation (in the range of ordinary temperature to about 50° C.), and it may be usually 5–90% by weight, preferably 5–80% by weight. In such a range of concentration, the said solution has a low liquid viscosity and can usually be handled without any trouble.

In the process of the present invention, aryl vinyl sulfone solutions with 99% or higher ratios of aryl vinyl sulfones to the components except the solvent(s) in the analytical chromatogram (i.e., aryl vinyl sulfones with 99% or higher purity) can be obtained, and they can be used as intermediates of drugs or other products without any trouble.

The aryl vinyl sulfones in such solutions are sufficiently stable under the conditions and atmosphere in! which aryl vinyl sulfones are usually handled, such as for usage, storage, or transportation, and there will be no problems for their practical use.

The handling of purified aryl vinyl sulfones obtained by the production process of the present invention gives no trouble as compared with the handling work in powder form and makes it possible to keep at low levels the concentrations of aryl vinyl sulfones in the working atmosphere. Work can be done in the atmosphere hardly causing exposure to aryl vinyl sulfones.

In this manner, purified aryl vinyl sulfone solutions can be produced by the crystallization of aryl vinyl sulfones from aryl vinyl sulfone-containing solutions before purification, which can be obtained by various reactions; separation of solutions from the crystallization mixtures to obtain wet cakes of the aryl vinyl sulfones; and dissolution of these cakes in solution-forming solvents.

EFFECTS OF THE INVENTION

According to the process of the present invention, purified aryl vinyl sulfone solutions can be obtained, without no trouble, such as dusting, from the viewpoint of working atmosphere because of an absence of handling in solid form, and under an atmosphere in which the concentrations of aryl vinyl sulfones in the air are lowered over a working area for the production of aryl vinyl sulfones and handing the same. Further, the aryl vinyl sulfone solutions obtained are easy to handle, suitable for storage and also for transportation. They further have good aryl vinyl sulfone purity and can be used as synthetic materials of drugs or other products without any trouble.

EXAMPLES

The present invention will hereinafter be further illustrated by some examples; however, the present invention is not limited thereto.

Example 1

To 40.02 parts by weight of 2-(phenylsulfonyl)ethanol (97.29% purity) were added 18.60 parts by weight of toluene and then 0.83 part by weight of pyridine, and the mixture was warmed to an internal temperature of 60° C., after which 28.82 parts by weight of thionyl chloride was added dropwise at 60–70° C. over 5 hours. The mixture was then kept with stirring at an internal temperature of 70° C. for 3 hours. After the end of temperature keeping, 40.0 parts by weight of toluene was added, and the mixture was cooled to an internal temperature of 45° C., after which the reaction mass was added dropwise to a mixed solution containing 85.0 parts by weight of 7% aqueous sodium bicarbonate solution and 54.4 parts by weight of toluene. After stirring, the mixture was left undisturbed and treated by phase separation to give an organic layer. To the organic layer was added 86.1 parts by weight of 7% aqueous sodium bicarbonate solution, and the mixture was treated by washing and phase separation.

To the organic layer treated by washing was then added 1.04 parts by weight of triethylamine, and the mixture was warmed to an internal temperature of 60° C., after which 25% aqueous potassium carbonate solution was added dropwise at 60° C. for 3 hours. After the end of dropwise addition, the mixture was further kept with stirring at an internal temperature of 60° C. for 5 hours. The mixture was cooled to room temperature, and an aqueous layer was removed by phase separation. An organic layer was treated by washing twice with 5% aqueous sulfuric acid solution, and then treated by washing 15.9 parts by weight of 1% aqueous sodium bicarbonate solution, and further treated by washing with 15.9 parts by weight of water, thereby obtaining a toluene solution of phenyl vinyl sulfone.

From the solution obtained, some of toluene was removed by distillation for adjustment such that the: concentration of phenyl vinyl sulfone came to 43%, after which the said concentrated solution was added dropwise into 68.4 parts by weight of hexane at an internal temperature of 20–30° C. over 1 hour. After the end of dropwise addition, the mixture was cooled to an internal temperature of −10° C., and the resulting slurry of phenyl vinyl sulfone crystals was transferred to a filtering module and filtered in a closed system, after which the phenyl vinyl sulfone crystals were washed with 161.1 parts by weight of hexane. To the phenyl vinyl sulfone crystals in the filtering module was added 137.2 parts by weight of acetonitrile, whereby the phenyl vinyl sulfone crystals were dissolved in the filtering modules. The resulting solution was transferred to a concentration vessel, and the hexane contained in the solution was removed by azeotropy with the acetonitrile, at an internal temperature of 60° C. under an operational pressure of 300 mmHg, thereby obtaining 100.0 parts by weight of 30.0% acetonitrile solution of phenyl vinyl sulfone. The purity of phenyl vinyl sulfone after removal of the solvent acetonitrile was 99.7%.

The purity analysis was carried out using gas chromatography under the following conditions:

Apparatus: GC-17A (Shimadzu)

Column: BP-1,0.25 $\mu$m, 0.22 mm$\phi$×25 m (SGE)

Carrier gas: helium

Flow rate: 15 psi. (103 kPa)

Split flow: 50 ml/min.

Inlet temperature 300° C.

Detector: FID 320° C.

Column oven: 100° C. −10° C./min. −320° C. (5 minutes)

Reference Example 1
Measurement of Concentration in the Air During the Handling of an Aryl Vinyl Sulfone Solution A phenyl vinyl sulfone/acetonitrile solution (concentration, 31.7% by weight; temperature, 40° C.) in a reaction vessel was drawn into another vessel by opening a bottom drawing cock of the reaction vessel. The concentration of phenyl vinyl sulfone in the air over a working area during this drawing work (an area within a distance of 100 cm from the drawing site) was measured to be 0.01 mg/m$^3$ at the maximum.

Comparative Example 1
Measurement of Concentration in the Air During the Handling of an Aryl Vinyl Sulfone Powder At room temperature, a reaction vessel was charged with 65 parts by weight of acetonitrile and then with 34.8 parts by weight of phenyl vinyl sulfone in powder form. The concentration of phenyl vinyl sulfone in the air over a working area during this charging work (an area within a distance of 100 cm from the charging site) was measured to be 0.12 mg/m$^3$ at the maximum. As compared with the work of handling a phenyl vinyl sulfone solution, the concentration of phenyl vinyl sulfone in the air was about 10 times as large as that one.

Reference Example 2
Stability of Aryl Vinyl Sulfone/acetonitrile Solution

About 70 ml of a phenyl vinyl sulfone/acetonitrile solution (phenyl vinyl sulfone concentration, 30%) and a chip of stainless steel (20 mm×25 mm×2 mm) (assuming the storage in a stainless steel vessel) were put in a glass sample tube of 100 ml in volume, which was purged with nitrogen gas and then sealed with a tight stopper, followed by stability tests in a thermostatic bath at 40° C. The results of retention are shown in Table 1. The concentration of phenyl vinyl sulfone in the phenyl vinyl sulfone/acetonitrile solution was analyzed by gas chromatography.

TABLE 1

| Elapsed days | 0 day | 30 days | 60 days | 90 days |
| --- | --- | --- | --- | --- |
| Retention | 100% | 100% | 99.9% | 99.4% |

Reference Example 3
Stability of Aryl Vinyl Sulfone Solutions

About 35 ml of a phenyl vinyl sulfone solution and a chip of stainless steel (20 mm×25 mm×2 mm) (assuming the storage in a stainless steel vessel) were put in a glass sample tube of 50 ml in volume, which was purged with nitrogen gas and then sealed with a tight stopper, followed by stability tests in a thermostatic bath at 40° C. The results of retention when a toluene solution (concentration, 30%), a methyl isobutyl ketone solution (concentration, 30%), and a methyl t-butyl ether solution (concentration, 10%) were used as the phenyl vinyl sulfone solutions are shown in Table 2.

The concentration of phenyl vinyl sulfone in each solution was analyzed by gas chromatography. In the table, MIK refers to methyl isobutyl ketone; and MTBE, methyl t-butyl ether.

TABLE 2

| Elapsed days | 0 day | 15 days |
| --- | --- | --- |
| Retention in toluene solution | 100% | 100% |
| Retention in MIK solution | 100% | 99.5% |
| Retention in MTBE solution | 100% | 100% |

Comparative Example 2

Stability tests were carried out in the same manner as described in Reference Example 3, except that an ethanol solution (concentration, 10%) and an N,N-dimethylformamide solution (concentration, 30%) were used as the phenyl vinyl sulfone solutions. The results of retention were shown in Table 3. In the table, DMF refers to N,N-dimethylformamide.

For the DMF solution, yellow coloring was observed with the lapse of storage days.

TABLE 3

| Elapsed days | 0 day | 15 days |
| --- | --- | --- |
| Retention in ethanol solution | 100% | 83.8% |
| Retention in DMF solution | 100% | 99.0% |

Example 2

An acetone solution of the purified aryl vinyl sulfone is obtained using diisopropyl ether instead of hexane as the washing solvent and using acetone instead of acetonitrile as the solution-forming solvent in the process of Example 1.

Example 3 a chloroform solution of the crude aryl vinyl sulfone is obtained using chloroform instead of toluene in example 1, followed by crystallization, and a chloroform solution of the purified aryl vinyl sulfone is obtained using chloroform instead of acetonitrile as the solution-forming solvent.

What is claimed is:

1. A process for producing a purified aryl vinyl sulfone solution, which comprises the steps of:
   (a) subjecting a crude aryl vinyl sulfone solution in an organic solvent to crystallization to obtain a crystallization mixture,
   (b) dissolving a wet cake separated from the crystallization mixture in a solvent selected from an ether of 4 to 8 carbon atoms, an aromatic hydrocarbon of 6 to 10 carbon atoms, a halogenated hydrocarbon of 1 to 6 carbon atoms, a ketone of 3 to 8 carbon atoms, an ester of 3 to 6 carbon atoms and a nitrile of 2 to 6 carbon atoms.

2. The process according to claim 1, wherein an aliphatic hydrocarbon of 5 to 10 carbon atoms is mixed with the crude aryl vinyl sulfone solution in the crystallization step (a).

3. The process according to claim 1, wherein the wet cake separated from the crystallization mixture is washed with the organic solvent used in step (a), the solvent selected in step (b), or an aliphatic hydrocarbon of 5 to 10 carbon atoms before being dissolved in step (b).

4. The process according to claim 2 or 3, wherein the organic solvent in step (a) or the aliphatic hydrocarbon of 5 to 10 carbon atoms is a solvent having a lower boiling point than that of the solvent that dissolves the wet cake in step (b) or is a solvent that forms an azeotropic mixture with the solvent used in step (b) to dissolve the wet cake.

5. The process according to claim 4, which further comprises the step of concentrating the aryl vinyl sulfone solution obtained in step (b), thereby the organic solvent used in step (a) or the aliphatic hydrocarbon of 5 to 10 carbon atoms is removed therefrom.

6. The process according to claim 1, wherein the step (a) and (b) are carried out in a closed system.

7. The process according to claim 1, wherein the aryl vinyl sulfone is a compound of formula (III):

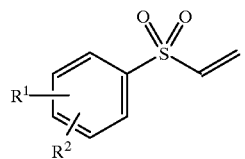

(III)

wherein R1 and R2 are the same or different and are independently a hydrogen atom, a halogen atom, a lower alkyl, lower alkoxy, nitro, amino, lower alkylamino, or di(lower alkyl)amino group.

8. The process according to claim 7, wherein the crude aryl vinyl sulfone is a compound obtained by reacting a compound of formula (I):

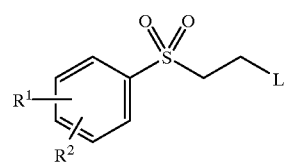

(I)

wherein R1 and R2 are the same as defined in connection with formula (III), and L is a leaving group, with a base: or is a compound obtained by the oxidation of an aryl vinyl sulfide compound of formula (II):

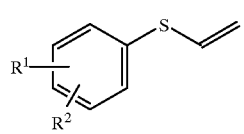

(II)

wherein R1 and R2 are the same as defined above.

9. The process according to claim 8, wherein the leaving group L is a halogen atom, a sulfate, nitrate or sulfonyloxy group.

* * * * *